United States Patent [19]

Ishiwara et al.

[11] Patent Number: 5,106,360
[45] Date of Patent: Apr. 21, 1992

[54] THERMOTHERAPEUTIC APPARATUS

[75] Inventors: Koichiro Ishiwara; Shinji Hatta; Masashi Abe, all of Tokyo, Japan

[73] Assignee: Olympus Optical Co., Ltd., Tokyo, Japan

[21] Appl. No.: 657,331

[22] Filed: Feb. 11, 1991

Related U.S. Application Data

[63] Continuation of Ser. No. 241,720, Sep. 8, 1988, abandoned.

[30] Foreign Application Priority Data

Sep. 17, 1987 [JP] Japan .......................... 62-141974[U]
Sep. 29, 1987 [JP] Japan .......................... 62-245514
Apr. 6, 1988 [JP] Japan ............................ 63-45648[U]

[51] Int. Cl.[5] .............................................. A61N 5/02
[52] U.S. Cl. ............................................ 600/2; 600/3; 128/786; 128/401
[58] Field of Search ................ 600/2, 3, 6; 128/784, 128/786, 787, 788, 804, 401

[56] References Cited

U.S. PATENT DOCUMENTS

| | | | |
|---|---|---|---|
| 1,786,373 | 12/1930 | Walker | 600/2 |
| 3,872,856 | 3/1972 | Clayton | 606/6 |
| 4,292,960 | 10/1981 | Paglione | 600/2 |
| 4,676,258 | 6/1987 | Inokuchi et al. | |

Primary Examiner—Lee S. Cohen
Assistant Examiner—John P. Lacyk
Attorney, Agent, or Firm—Firishauf, Holtz, Goodman & Woodward

[57] ABSTRACT

A thermotherapeutic apparatus comprises an internal applicator adapted to be inserted into a body cavity of a patient. The internal applicator includes an electrode for warming the tissues of the patient's body with use of an applied voltage, a holding member for holding the electrode, a balloon surrounding the electrode and attached to the holding member, a feed/discharge unit for feeding into and discharging a fluid from the balloon, and a mechanism for situating a radiation source, used in radiotherapy on the body tissues, in the vicinity of the electrode.

24 Claims, 10 Drawing Sheets

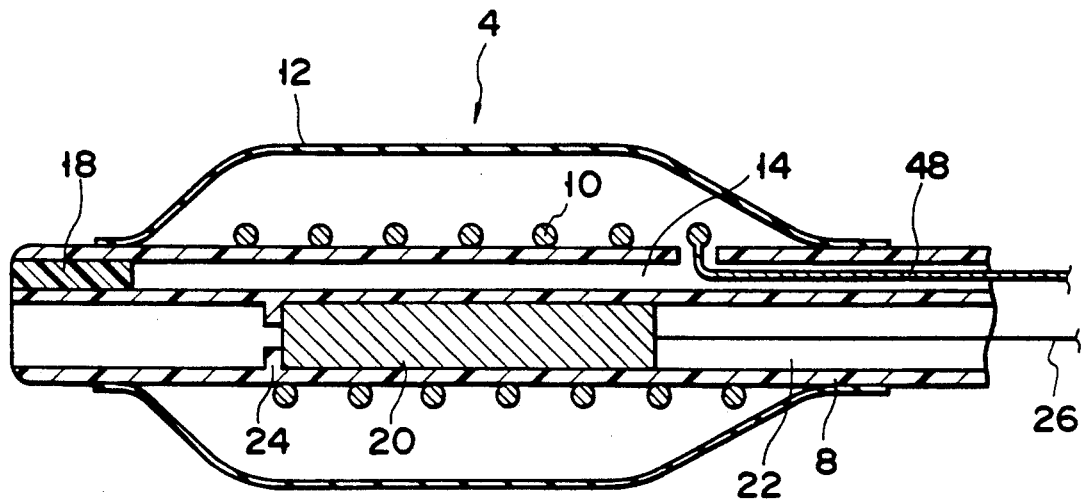
F I G. 1
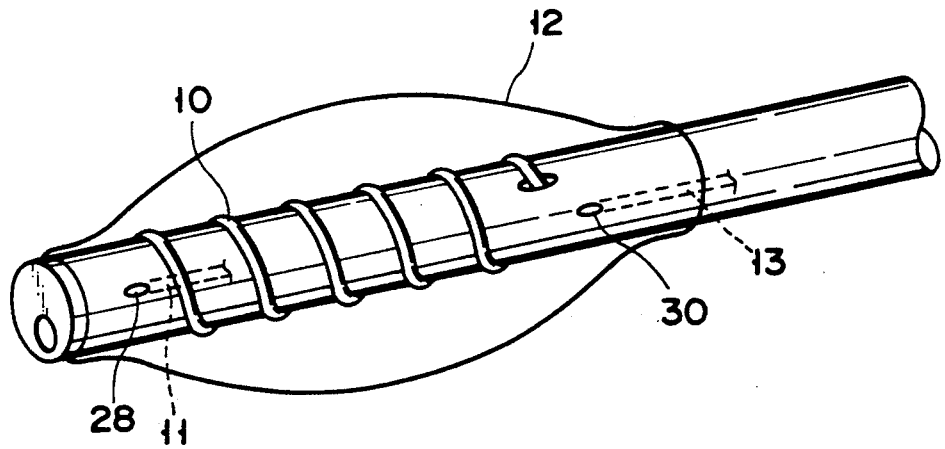
F I G. 2

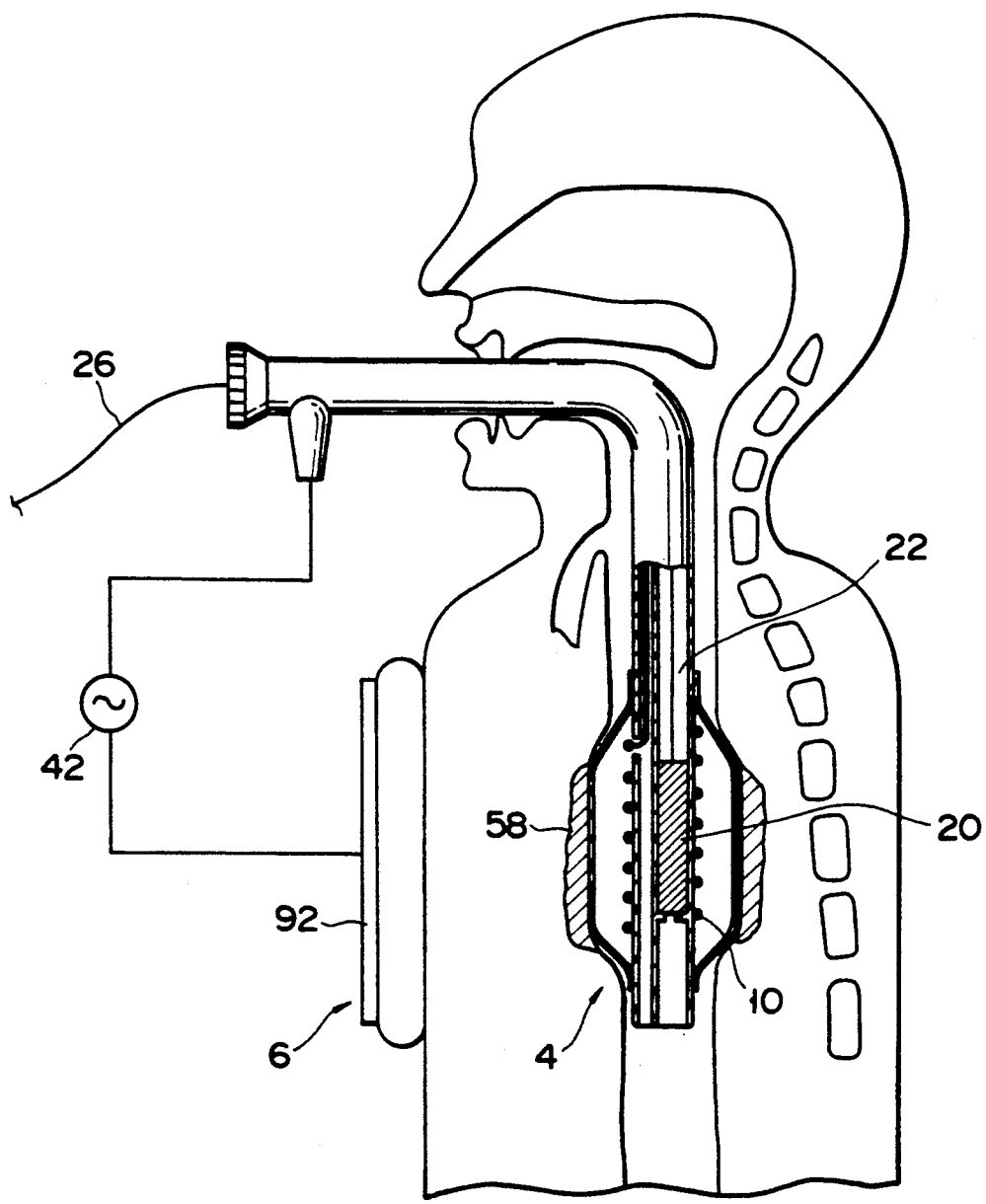
F I G. 4

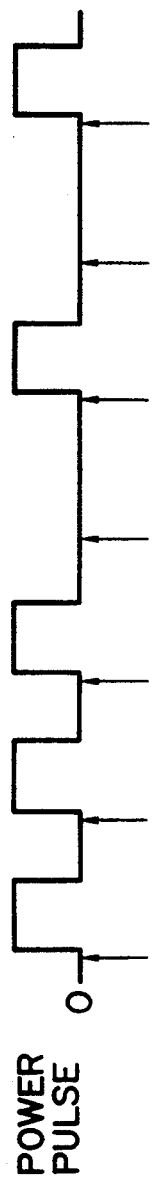
F I G. 9A POWER PULSE
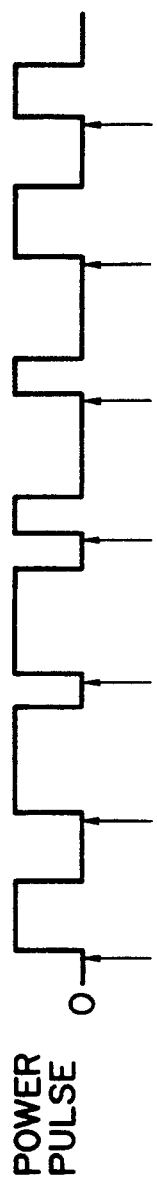
F I G. 9B POWER PULSE
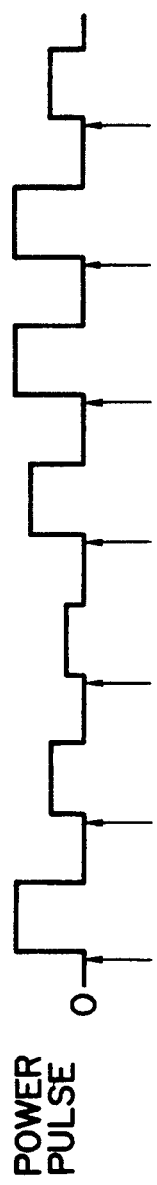
F I G. 9C POWER PULSE
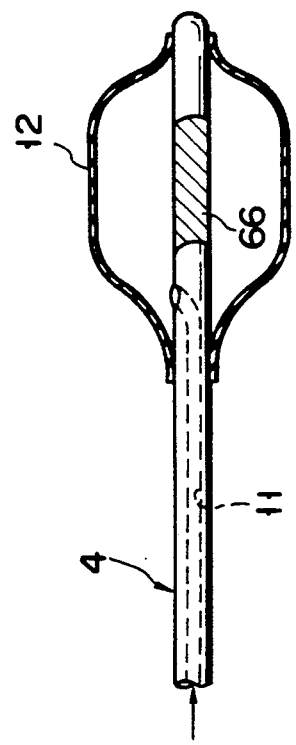
F I G. 10

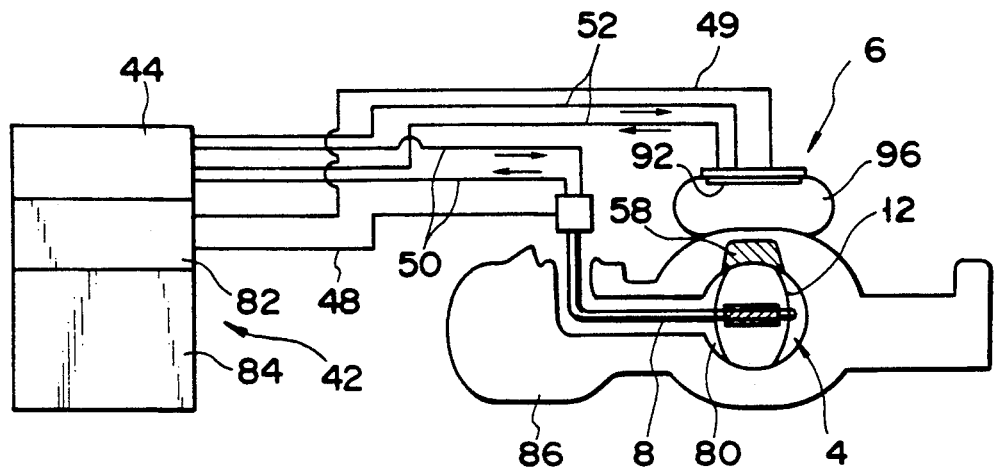
F I G. 11
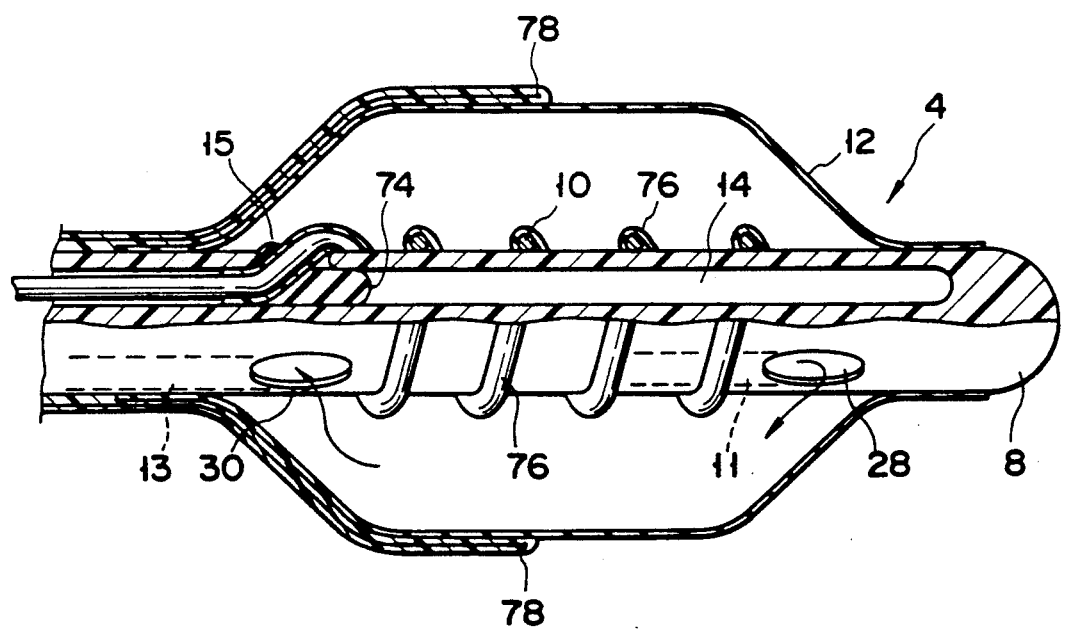
F I G. 12

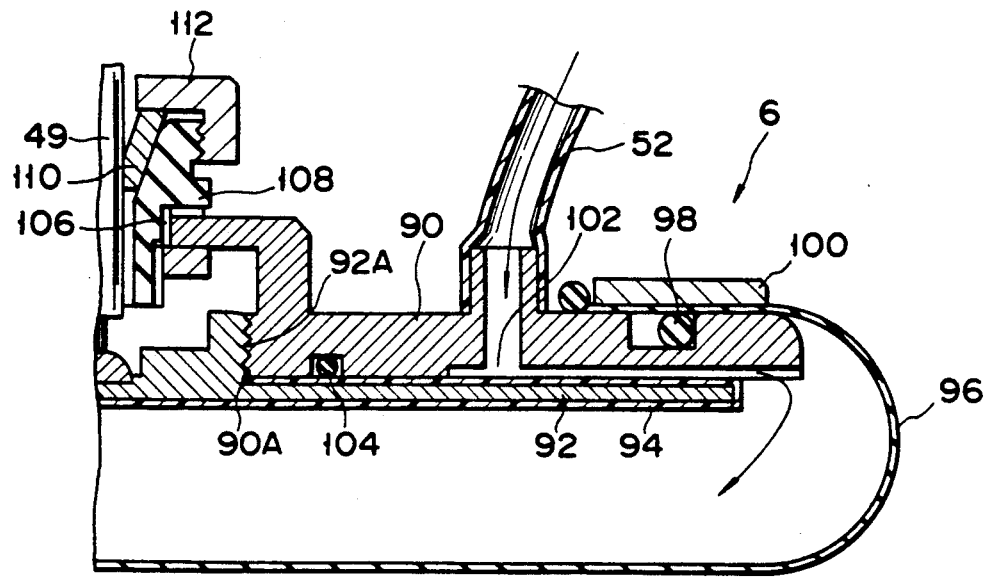
F I G. 13
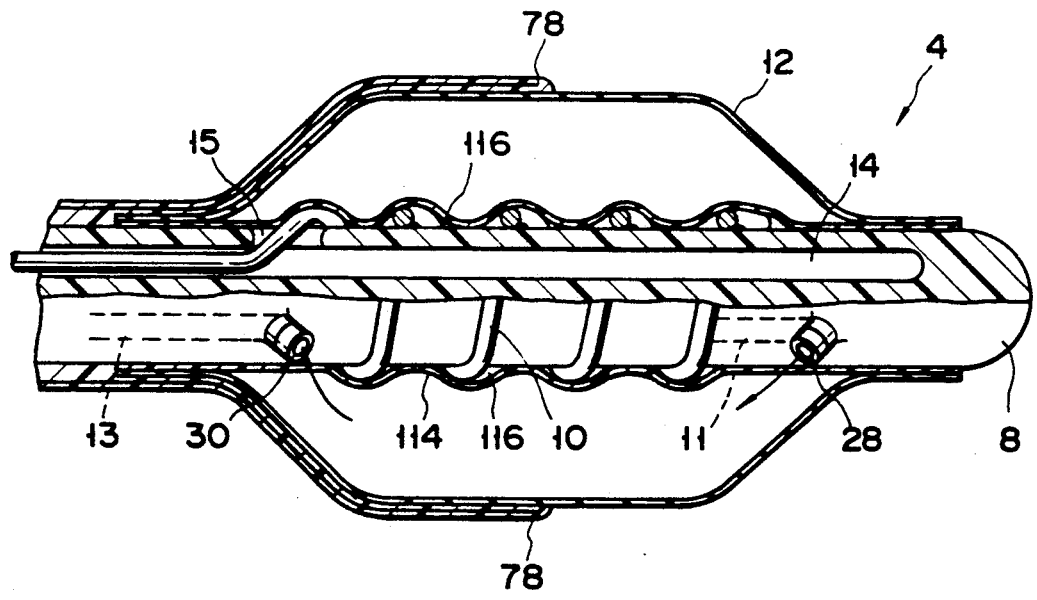
F I G. 14

THERMOTHERAPEUTIC APPARATUS

This application is a continuation of application Ser. No. 07/241,720 filed Sept. 8, 1988 now abandoned.

BACKGROUND OF THE INVENTION

1. Field of the Invention

The present invention relates to a thermotherapeutic apparatus for curing affected parts inside a patient's body.

2. Description of the Related Art

Thermotherapy is a method of curing cancer which has recently come to public notice. In this treatment, a curer warms the affected part to about 43° C. to kill cancerous cells, knowing that the cancerous cells can be more easily destroyed by heat than normal cells. Disclosed in Japanese Patent Disclosure (KOKAI) No. 60-119962, for example, is a thermotherapeutic apparatus which comprises one external electrode and one internal electrode. This typical thermotherapeutic apparatus is designed so that the internal electrode is inserted into that region of a patient's body cavity which faces a tumor, while the external electrode is set on the outside of the patient's body so as to face the internal electrode across the tumor. A high-frequency oscillator is used to apply a high-frequency voltage between these two electrodes, thereby subjecting the affected part to high-frequency energy. By doing this, the tumorous region can be inductively warmed. Since the internal electrode is adapted to be inserted into the body cavity, its surface is narrower than that of the external electrode, so that the density of the high-frequency energy applied increases as the internal electrode is approached.

Accordingly, the thermotherapeutic apparatus is an effective means of local warming. It is generally known, however, that thermotherapy can enjoy improved efficacy if it is combined with radiotherapy or chemotherapy. Conventionally, therefore, thermotherapy is effected in combination with radiotherapy or chemotherapy. In a typical method of radiotherapy, radiation is applied from outside a patient's body. In this case, however, if the affected part is situated deep in the body, the patient will probably be subjected to general exposure due to excessive irradiation, thus suffering damage to his body.

A new method has recently been proposed to prevent increase of the total amount of irradiation and to apply radiation directly to the affected part of a patient's body. According to this method, a very small radiation source (radiation seed) is made to indwell in the vicinity of the affected part for a limited period of time, by needling or the like. If the affected part is situated close to the body cavity, in particular, the radiation source is introduced into the cavity by using a catheter or the like.

Disclosed in Japanese Patent Disclosure (KOKAI) No. 58-78654 is a catheter which is adapted for localizing diathermic therapy using a radioisotope. With use of this catheter, diathermic therapy and radiotherapy can be exercised simultaneously.

When combining thermotherapy and radiotherapy, however, a plurality of catheters and internal electrodes are retained in the body cavity for a long period of time, so that a patient must stand a great pain. In the treatment method stated in Japanese Patent Disclosure No. 58-78654, moreover, normal tissues will be also exposed to excessive radiation if a radiation source is made to indwell in the body cavity for prolonged thermotherapy.

SUMMARY OF THE INVENTION

The object of the present invention is to provide a thermotherapeutic apparatus which can simultaneously perform thermotherapy and radiotherapy to cure a tumor, thus ensuring improved remedial value, shorter treatment time, shorter irradiation time, and relief of a patient's pain.

The above object of the invention is achieved by a thermotherapeutic apparatus constructed as follows. The apparatus comprises an internal applicator adapted to be inserted into a body cavity of a patient. The internal applicator includes an electrode for warming the tissues of the patient's body with use of an applied voltage, a holding member for holding the electrode, a balloon surrounding the electrode and attached to the holding member, a feed/discharge unit for feeding into and discharging a fluid from the balloon, and a mechanism for situating a radiation source, used in radiotherapy on the body tissues, in the vicinity of the electrode.

The thermotherapeutic apparatus according to the present invention can simultaneously perform thermotherapy and radiotherapy on local tissues of a living body, thereby reducing the treatment time and causing less pain to the patient.

In the thermotherapeutic apparatus of the invention, moreover, the radiation source can be freely loaded into or removed from the applicator in a short time, so that the patient can be protected against exposure to excessive radiation.

BRIEF DESCRIPTION OF THE DRAWINGS

FIGS. 1 and 2 are a longitudinal section view and a perspective view, respectively, showing an internal applicator of a thermotherapeutic apparatus according to a first embodiment of the present invention;

FIG. 4 is a schematic view showing the manner of joint use of internal and external applicators;

FIGS. 9A, 9B and 9C are graphs illustrating output pulses and the timing for temperature detection in the electric circuits shown in FIGS. 6, 7 and 8, respectively;

FIG. 10 is a schematic view of an internal applicator according to the second embodiment;

FIG. 11 is a side view schematically showing a thermotherapeutic apparatus according to a third embodiment of the present invention;

FIG. 12 is a partial sectional view of the internal applicator according to the third embodiment;

FIG. 13 is a longitudinal sectional view showing part of an external applicator according to the third embodiment;

FIG. 14 is a partial sectional view showing a modification of the internal applicator according to the third embodiment;

DETAILED DESCRIPTION OF THE PREFERRED EMBODIMENTS

Figure 3:
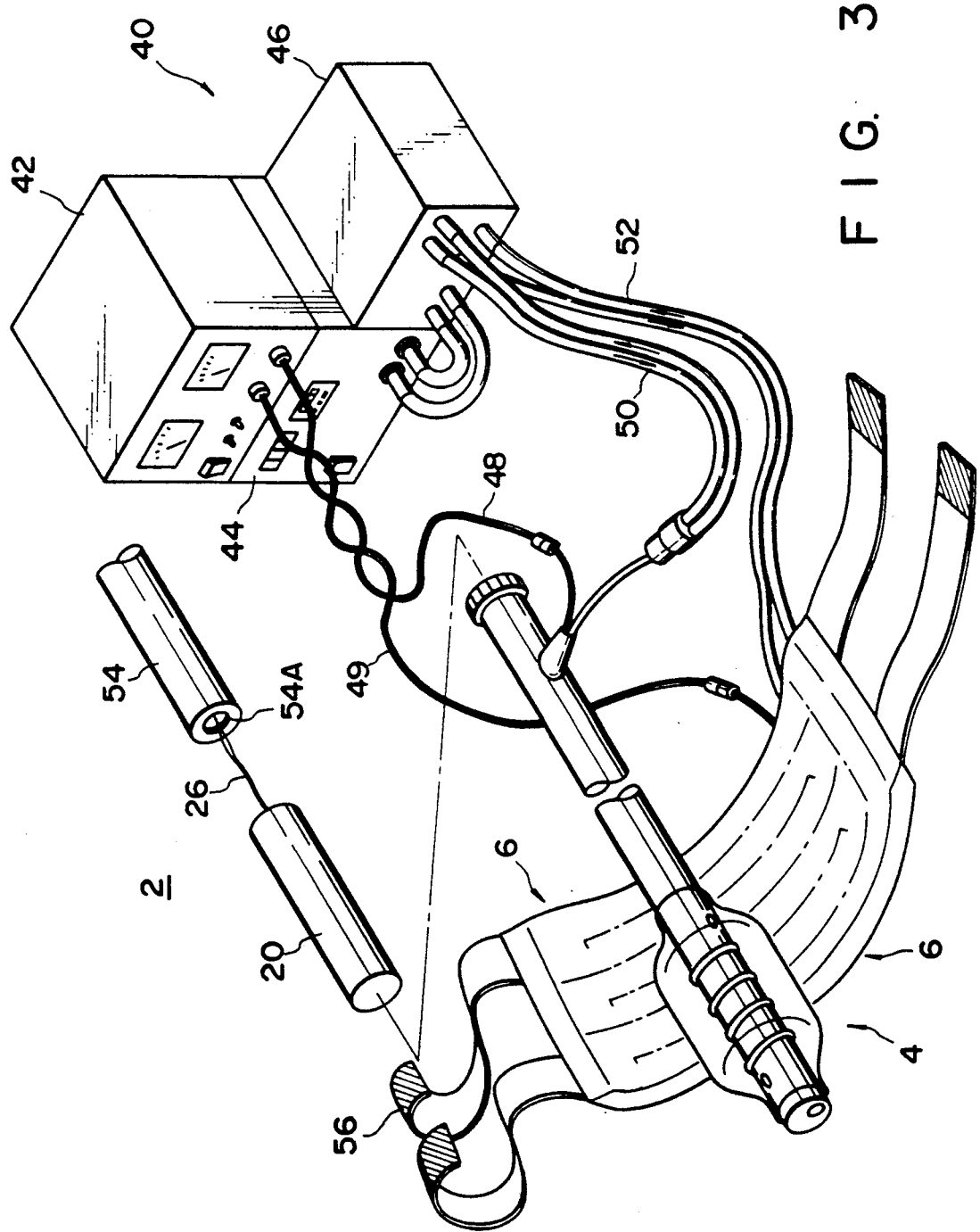
FIG. 3 is a perspective view showing a system of the thermotherapeutic apparatus according to the first embodiment of the invention.

Preferred embodiments of the present invention will now be described in detail with reference to the accompanying drawings.

FIGS. 1 and 2 show internal applicator 4 of a thermotherapeutic apparatus according to a first embodiment of the present invention. Applicator 4 includes porous tube (multi-lumen tube) 8 which has a plurality of passages extending in the axial direction. Tube 8 is formed of soft resin such as polyurethane. Coil-shaped RF electrode 10 and balloon 12 covering the same are attached to the distal end portion of tube 8 by means of a bonding agent or by stringing. Power cable 48 is inserted in power cable passage 14 among the other axial passages of porous tube 8. The leading end of cable 48 is connected to RF electrode 10 which is coiled around tube 8. The trailing end of cable 48 is connected to RF oscillator 42 shown in FIG. 3. The distal end of passage 14 is closed by means of sealing member 18.

Porous tube 8 also has insertion passage 22 extending along the axial direction thereof. Substantially cylindrical radiation source 20, such as iridium (Ir), is slidably inserted in passage 22. Formed at the distal end of passage 22 is narrow retaining portion 24 for situating radiation source 20 in the vicinity of RF electrode 10. Strayproof string 26 for removal is attached to the trailing end of radiation source 20. The radiation source can be removed from porous tube 8 by pulling the free end portion of string 26.

Porous tube 8 has passages 11 and 13 for expanding balloon 12 and circulating a liquid, besides power cable passage 14 and insertion passage 22. Liquid feed port 28 and discharge port 30 are formed individually at the respective distal ends of these circulation passages so as to communicate with the inside of balloon 12. The internal body wall touched by balloon 12 can be warmed or cooled by circulating the liquid through the balloon. The respective proximal ends of the circulation passages are connected to heat exchanger 46.

The system of the thermotherapeutic apparatus according to the first embodiment will now be described. This system comprises internal applicator 4, external applicator 6, and control unit 40. Unit 40 includes RF oscillator 42, thermostatic circulator 44, and heat exchanger 46. Electrode 10 of internal applicator 4 is connected to oscillator 42 by means of power cable 48 which diverges from the proximal end portion of porous tube 8. The respective other ends of passages 11 and 13 for balloon expansion and fluid circulation are connected to heat exchanger 46 by means of tubes 50.

Exchanger 46 is connected to circulator 44. Thus, the temperature of the fluid is kept constant. External applicator 6, on the other hand, has flexible external electrode 92 (FIG. 4) and a passage through which a refrigerant flows. As in the case of internal applicator 4, electrode 92 is connected to RF oscillator 42 by means of power cable 49, and the refrigerant passage is connected to heat exchanger 46 by means of tubes 52. External applicator 6 is fitted with fixing belt 56 which is adapted to be wound around, e.g., the trunk of a patient. As shown in FIG. 3, radiation source 20 is guided to the distal end portion of internal applicator 4 by being pushed by means of push rod 54 inserted through the proximal end of tube 8. Bore 54A is formed in the distal end of rod 54, and string 26 attached to the trailing end of radiation source 20 is passed through the bore.

The following is a description of the operation of the thermotherapeutic apparatus according to the first embodiment. First, internal applicator 4 is inserted into a region of the body cavity in the vicinity of tumor 58, such as a carcinoma, on the internal body wall so that RF electrode 10 is located beside the affected part, as shown in FIG. 4. Then, water is poured through tube 50 into balloon 12 from feed port 28, thereby bringing the balloon into intimate contact with the body wall and fixing applicator 4. Thereafter, RF electromagnetic waves are applied between internal and external electrodes 10 and 92 on either side of the affected part, thereby warming the affected part.

Before or during thermotherapy, radiation source 20 is inserted, as required, into insertion passage 22 by means of push rod 54 so that it reaches retaining portion 24. After it is left in the body for a proper period of time, source 20 is removed by pulling string 26. Meanwhile, RF electrode 10 is left as it is, for continued thermotherapy.

With use of the thermotherapeutic apparatus according to the first embodiment, as described above, the tumor in the body cavity can be simultaneously subjected to both thermotherapy and radiotherapy, thus obtaining a great curing effect in a short period of time. Since radiation source 20 can be easily removed from the patient's body, moreover, the patient is less likely to be exposed to excessive radiation.

Figure 5:
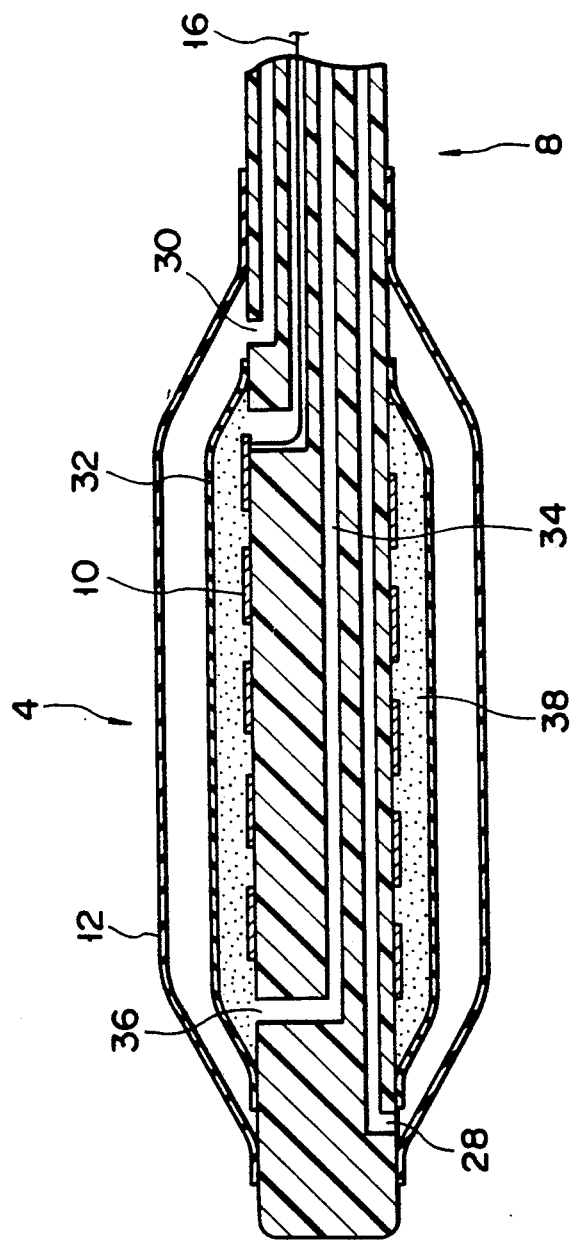
FIG. 5 is a longitudinal sectional view showing a modification of the internal applicator according to the first embodiment.
Figure 6:
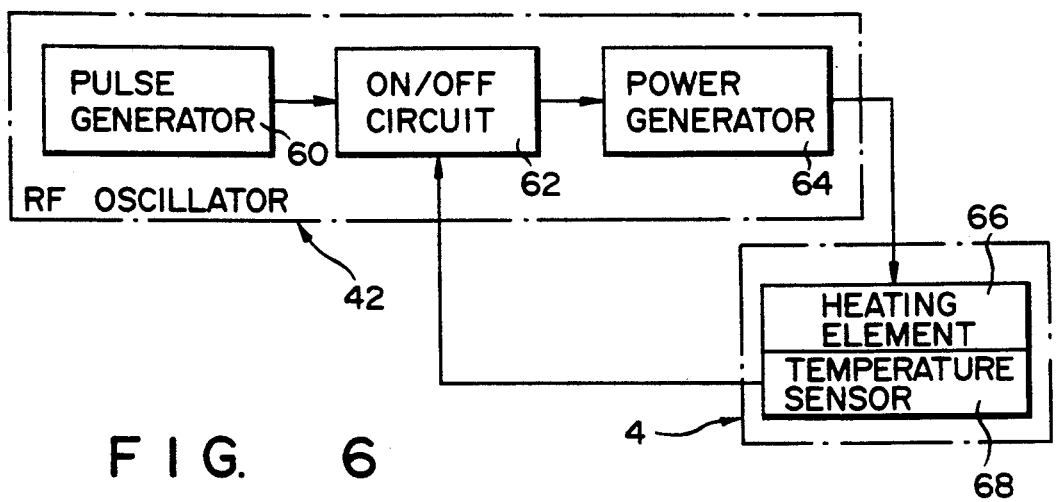
FIG. 6 is a block diagram showing an electric circuit of a thermotherapeutic apparatus according to a second embodiment of the present invention.

FIG. 5 shows a modification of the internal applicator according to the first embodiment of the present invention. In this modification, second balloon 32 is interposed between balloon 12 and RF electrode 10. Passage 34 and feed port 36, through which a fluid is to be injected into balloon 32, are provided independently of feed port 28 and discharge port 30 which communicate with the inside of balloon 12. The proximal end of fluid injection passage 34 is connected to a pump (not shown). Liquid radiation source 38, which is a suspension of radiation material particulates in a liquid body, is injected through feed port 36 into second balloon 32 to fill it up.

In the thermotherapeutic apparatus according this modification, the quantity of radiation source 38 near the affected part can be freely adjusted as required. Due to the use of the liquid radiation source, moreover, the distal end of the electrode of the internal applicator can never lose its flexibility. Furthermore, the liquid radiation source can be easily injected into and discharged from the balloon.

FIGS. 6 to 10 show a thermotherapeutic apparatus according to a second embodiment of the present invention. The apparatus of this embodiment comprises RF oscillator 42 and internal applicator 4. Oscillator 42 includes pulse generator 60, ON/OFF circuit 62, and power generator 64. Applicator 4 is provided with heating element 66 and temperature sensor 68. In this second embodiment, a pulse signal from pulse generator 60 is supplied through ON/OFF circuit 62 to power generator 64. Generator 64 supplies pulse power to heating element 66 in synchronism with the input pulses. The temperature of element 66, thus supplied with the pulse power, is detected by means of temperature sensor 68. The output of sensor 68 is fed back to ON/OFF circuit 62. Sensor 68 is situated in a position near element 66 such that it can indirectly detect the temperature of the affected part.

In this apparatus, if the heating temperature of heating element 66 detected by temperature sensor 68 is below a reference temperature, ON/OFF circuit 62 is caused to conduct. Accordingly, continuous pulses are supplied from pulse generator 60 to power generator 64, so that the pulse power is supplied to heating element 66. Thus, element 66 generates heat while the pulses are active and does not while the pulses are negative, so that the temperature is made uniform, that is, there is no temperature gradient, during the negative period.

When the attainment of the reference temperature is detected by temperature sensor 68, ON/OFF circuit 62 is cut off, so that the supply of the pulse power to heating element 66 is interrupted until the heating temperature detected by sensor 68 becomes lower than the reference temperature.

According to this embodiment, the heating temperature can be kept constant at a predetermined reference temperature by means of a simple circuit.

Figure 7:
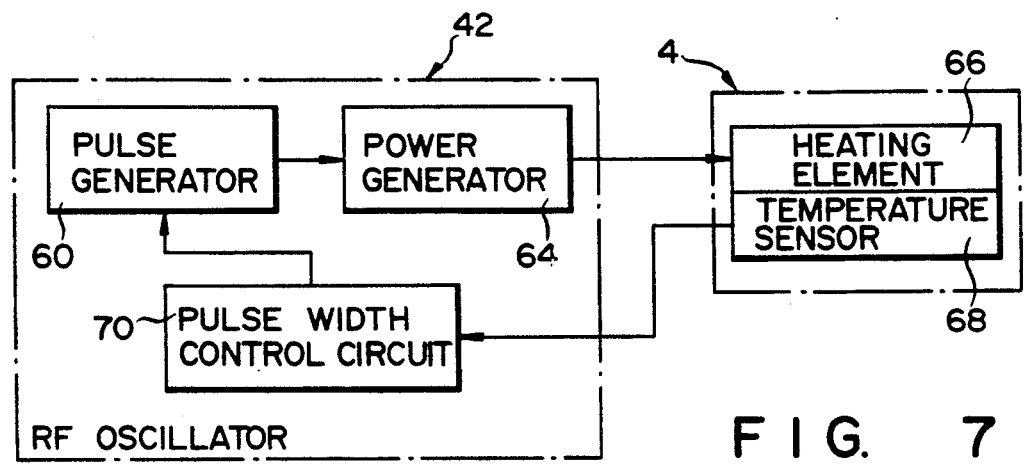
FIG. 7 is a block diagram showing a first modification of the electric circuit of the thermotherapeutic apparatus according to the second embodiment.

FIG. 7 shows a first modification of the second embodiment. This modification differs from the second embodiment in that pulse generator 60 is connected directly to power generator 64 without using the ON/OFF circuit, and that RF oscillator 42 is provided with pulse width control circuit 70 so that the output pulse width of generator 60 is feedback-controlled in accordance with the output of temperature sensor 68.

Thus, if the heating temperature of heating element 66 detected by temperature sensor 68 is lower than the predetermined reference temperature, the pulse signal delivered from pulse generator 60 is adjusted in accordance with the output of sensor 68 so that its active and negative periods are relatively long and short, respectively. When the reference temperature is attained, on the other hand, the active and negative periods are made relative short and long, respectively.

Thus, the heating temperature can be kept constant at the predetermined reference temperature by adjusting the pulse width of the power supplied to heating element 66, in accordance with the output of temperature sensor 68.

Figure 8:
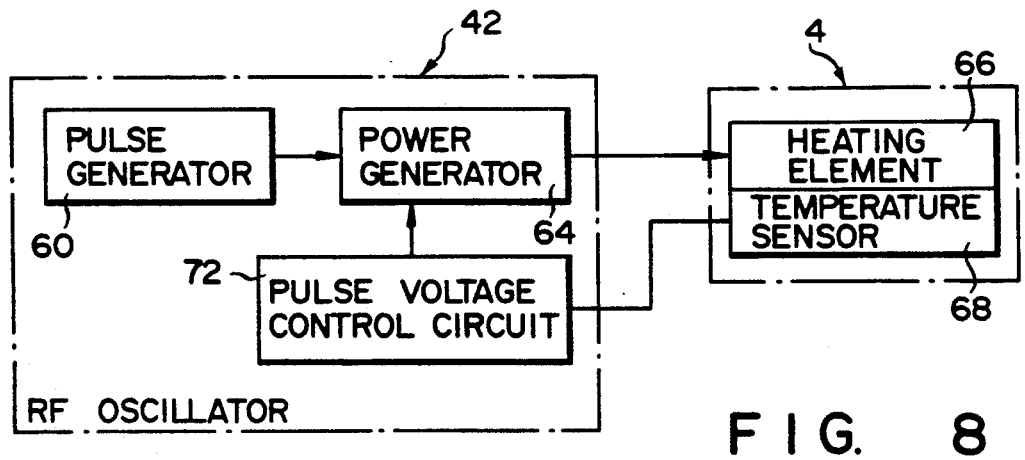
FIG. 8 is a block diagram showing a second modification of the electric circuit of the thermotherapeutic apparatus according to the second embodiment.

Although pulse width control circuit 70 is connected to pulse generator 60 in the first modification, it may alternatively be connected to power generator 64 so that generator 64 is feedback-controlled. FIG. 8 shows a second modification of the second embodiment. In this modification, RF oscillator 42 is provided with pulse voltage control circuit 72, whereby the voltage of the pulse power supplied from power generator 64 to heating element 66 can be adjusted in accordance with the output of temperature sensor 68. Thus, the pulse voltage is adjusted to a high level when the heating temperature is lower than the reference temperature. In the reference temperature state, the pulse voltage is adjusted to a low level.

Thus, the heating temperature can be kept at the predetermined reference temperature by adjusting the voltage of the pulse power supplied to heating element 66.

In the embodiment and the modifications described above, the temperature can be detected at all times or with a desired timing, by means of temperature sensor 68. Preferably, however, it should be detected immediately before the pulse power turns active, during the negative period, as shown in FIGS. 9A, 9B and 9C. If this is done, then the temperature can be detected in a state such that the temperature gradient produced by the pulse power supplied is reduced to its minimum. FIGS. 9A, 9B and 9C show power pulses obtained according to the second embodiment, the first modification thereof, and the second modification, respectively.

In the aforementioned embodiment and modifications, moreover, heating element 66 and temperature 68 are provided separately. When using an element having a temperature characteristic, e.g., a resistor, diode, Zener diode, etc., as the heating element, however, the element can double as a heat generating member and a temperature sensor. Thus, temperature information can be obtained by measuring a resistance value if the heating element used is a resistor; a forward voltage if the element is a diode, and a Zener voltage in the case of a Zener diode.

With such use of only one element for both heating element 66 and temperature sensor 68, the components used in the apparatus are reduced in number, so that the assembling work is simple, and the manufacturing costs are low.

Although the affected part may be heated directly by means of the heating element, heating element 66 may alternatively be disposed within balloon 12 of internal applicator 4, as shown in FIG. 10. In this case, gas or liquid is fed into balloon 12 through feed passage 11 of applicator 4, thereby bringing the balloon into contact with the tissues of the affected part. Then, the fluid in balloon 12 is heated by means of heating element 66 so that the affected part is indirectly warmed for thermotherapy. The temperature inside balloon 12 can be more quickly made uniform with use of a device for stirring the fluid in the balloon.

FIGS. 11 to 13 show a thermotherapeutic apparatus according to a third embodiment of the present invention. The thermotherapeutic apparatus according to this embodiment comprises internal and external applicators 4 and 6. As shown in FIG. 12, internal applicator 4 includes porous tube 8 which has electrode passage 14, feed passage 11, and discharge passage 13. A liquid, such as a physiological saline solution, is circulated through passages 11 and 13. Wire-shaped internal electrode 10 is inserted in electrode passage 14. The distal end portion of electrode 10 extends outward from electrode port 15 of passage 14, and the gap between electrode 10 and the peripheral edge of port 15 is sealed in a liquid-tight manner by means of seal member 74. Also, the distal end portion of electrode 10 is covered by coating 76 formed of, e.g., an electrically insulating paint, and is wound on the outer peripheral surface of tube 8.

Formed at the distal end of porous tube 8 are feed port 28 and discharge port 30 which communicate with feed passage 11 and discharge passage 13, respectively. The distal end portion of tube 8 is covered in a liquid-tight manner by internal balloon 12, which is formed of a flexible material. A plurality of temperature sensing elements 78 are arranged on the outer surface of balloon 12. They are used to detect the temperature at contact regions between balloon 12 and the wall of body cavity 80.

As shown in FIG. 11, internal electrode 10 is connected through matching circuit 82 to high-frequency power source 84 by means of cable 48. Also, feed passage 11 and discharge passage 13 are connected to thermostatic circulator 44 by means of tubes 50, individually. A physiological saline solution or other liquid, kept at a predetermined temperature, is fed from circulator 44 into feed passage 11. The liquid flows out from feed port 28 into internal balloon 12, flows into discharge passage 13 through discharge port 30, and then returns to thermostatic circulator 44. Thus, the liquid circulates through this course.

As shown in FIG. 13, external applicator 6 has body 90, and external electrode 92 is attached to the underside of body 90. Male screw portion 92A, which is formed in the central portion of electrode 92, threadedly engages female screw portion 90A of body 90. Like internal electrode 10, external electrode 92 is covered by electrically insulating coating 94. The underside of body 90 is enclosed by external balloon 96. The peripheral portion of balloon 96 is bonded to the top face of body 90 with O-ring 98 between them, and is kept liquid-tight by means of ring-shaped retainer 100. Body 90 is formed with liquid feed passage 102 and a drainage passage (not shown). One end of each of these passages communicates with the inside space of external balloon 96, while the other end thereof is connected with one end of its corresponding tube 52. The respective other ends of tubes 52 are connected to thermostatic circulator 44. The liquid kept at the predetermined temperature is fed from circulator 44 into external balloon 96.

O-ring 104 is interposed between body 90 and external electrode 92, whereby the liquid circulating through external balloon 96 is prevented from leaking through the engagement portion between female and male screw portions 90A and 92A.

Insertion portion 106 is formed at the central portion of the top face of body 90. It is penetrated by cable 49 which is connected to external electrode 92. Bush 108 is fitted in insertion portion 106, and cable 49 is passed through the bush and held in position by means of retaining member 110. Cable 49 is connected to high-frequency power source 84 through matching circuit 82. Cap 112 is screwed on bush 108.

The following is a description of the operation of the thermotherapeutic apparatus according to the third embodiment. First, internal applicator 4 is inserted into body cavity 80, and external applicator 6 is held against the outside of patient's body 86 so that the two applicators face each other across affected part 58 in body 86, as shown in FIG. 11.

Then, thermostatic circulator 44 and high-frequency power source 84 are actuated. Thereupon, the liquid circulates through internal and external balloons 12 and 96, the temperature at the contact regions between these balloons and patient's body 86 is kept constant, and a high-frequency voltage is applied between internal and external electrodes 10 and 92. As a result, affected part 58, situated between electrodes 10 and 92, is inductively warmed to a predetermined temperature for thermotherapy. Meanwhile, the temperature at the contact regions between internal balloon 12 and the wall of body cavity 80 is determined by means of temperature sensing element 78 in balloon 12. The output of high-frequency power source 84, for example, is adjusted so that power source 84 is controlled in accordance with a measurement signal from element 78, thereby keeping the temperature at the contact regions constant.

In the middle of thermotherapy, the liquid sometimes may leak from internal or external balloon 12 or 96 for various causes, thereby possibly entailing an accident from an electric shock.

In the thermotherapeutic apparatus according to this embodiment, however, electrodes 10 and 92 are covered by electrically insulating coatings 76 and 94, respectively, so that no electric shock can be caused even if the liquid leaks from balloon 12 or 96.

FIG. 14 shows a modification of internal applicator 4. In this modification, the whole distal end portion of porous tube 8 is covered by insulating film 114 formed of an electrical insulator sheet, so that internal electrode 10 is insulated from the liquid in internal balloon 12. The space between film 114 and the outer peripheral surface of tube 8 may be filled up with electrically conductive filler material 116. Also in this modification, an electric shock due to leakage of the liquid can be prevented.

Figure 15:
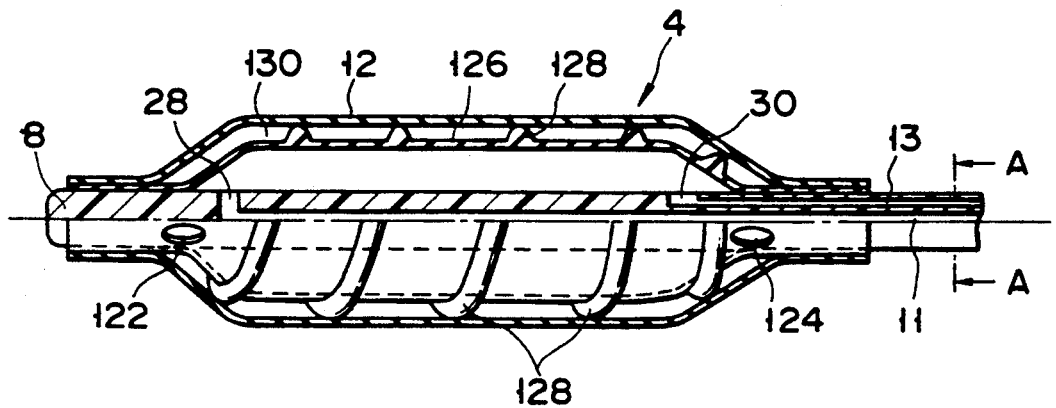
FIG. 15 is a partial sectional view showing an internal applicator of a thermotherapeutic apparatus according to a fourth embodiment of the present invention.
Figure 16:
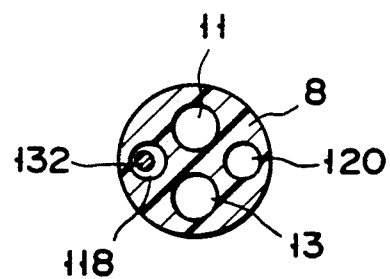
FIG. 16 is a cross-sectional view taken along line A-A of FIG. 15.

FIGS. 15 and 16 show internal applicator 4 of a thermotherapeutic apparatus according to a fourth embodiment of the present invention. Internal applicator 4 according to this fourth embodiment includes porous tube 8. As shown in FIG. 16, tube 8 has fluid feed passage 118 through which an electrode is passed, discharge passage 120, and feed and discharge passages 11 and 13 for a refrigerant, all these passages extending in the axial direction of the tube.

Refrigerant feed passage 11 communicates with first feed port 28 at the distal end portion of porous tube 8, discharge passage 13 connects with first discharge port 30 situated behind port 28. Ports 28 and 30 communicate with the inside space of flexible inner balloon (second balloon) 126, both ends of which are fixed in a liquid-tight manner to the outer peripheral surface of the distal end portion of tube 8. Spiral rib 128 is formed on the outer peripheral surface of balloon 126, whereby the second balloon is prevented from expanding beyond a predetermined outside diameter.

Inner balloon 126 is enclosed by outer balloon (first balloon) 12. Balloon 12 is fixed in a liquid-tight manner to both end portions of balloon 126. Thus, space 130 is defined between inner and outer balloons 126 and 12.

Fluid feed passage 118 communicates with second feed port 122 formed at the distal end portion of porous tube 8, while discharge port 124 connects with second discharge port 124 situated behind port 122. Ports 122 and 24 communicate with space 130 between first and second balloons 12 and 126. A liquid, such as a physiological saline solution, is injected from second feed port 122 into space 130 through passage 118 for the electrode. This liquid, which has good electrical conductivity, serves as an internal electrode. Moreover, fluid feed passage 118 is penetrated by electric wire 132 (FIG. 16) which is connected electrically with the liquid in space 130.

Electric wire 132 is connected to matching circuit 82 by means of cable 48, as shown in FIG. 11. Also, feed and discharge passages 11 and 13 for the refrigerant are connected to thermostatic circulator 44 by means of their corresponding tubes 50. The refrigerant, kept at a predetermined temperature, is fed from circulator 44 into passage 11. Thereafter, the refrigerant flows into inner balloon 126 via first feed port 28, and then flows out through first discharge port 30, thereby returning to thermostatic circulator 44. Thus, the refrigerant circulates through this course.

As shown in FIG. 11, external applicator 6 includes external balloon 96 and external electrode 92. Balloon 96 is connected to thermostatic circulator 44 by means of refrigerant feed and discharge tubes 52, and external electrode 92 is connected to matching circuit 82 by means of cable 49. Circuit 82 is connected to high-frequency power source 84, which applies a high-frequency voltage between external electrode 92 and the liquid electrode in space 130 of internal applicator 4.

The following is a description of the operation of the thermotherapeutic apparatus according to the fourth embodiment. First, internal applicator 4 is inserted into patient's body cavity 80, and external applicator 6 is held against the outside of the patient's body so that the two applicators face each other across affected part 58, as shown in FIG. 11. If thermostatic circulator 44 is actuated in this state, the refrigerant kept at the predetermined temperature circulates through inner balloon 126. In this case, balloon 126 is prevented from excessively expanding by rib 128.

While the refrigerant is circulated through inner balloon 126, an electrically conductive solution is injected into space 130 between inner and outer balloons 126 and 12 by means of a feeding device (not shown), e.g., a syringe. Thereupon, outer balloon 12 is brought into intimate contact with the inner wall surface of body cavity 80. If high-frequency power source 84 is actuated in this state, a high-frequency voltage is applied between inner and external applicators 4 and 6, thereby warming affected part 58.

In warming affected part 58, the conductive solution in space 130 is kept at a predetermined temperature by means of the refrigerant circulating through inner balloon 126. Thus, the affected part can be securely subjected to thermotherapy. Since the refrigerant circulates through the inner balloon which is situated inside space 130, moreover, the high-frequency voltage cannot be applied to the refrigerant. Thus, waste of high-frequency energy can be avoided, and the temperature of the refrigerant is prevented from excessively increasing.

Figure 17:
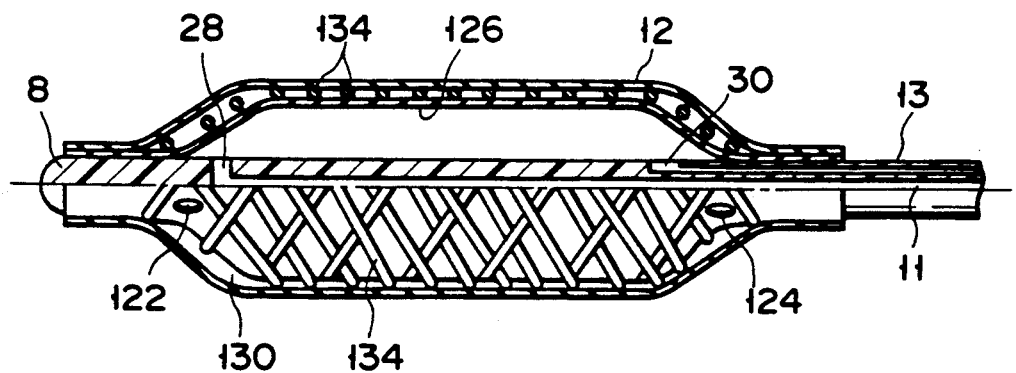
FIG. 17 is a partial sectional view showing a first modification of the internal applicator according to the fourth embodiment.

FIG. 17 shows a first modification of the internal applicator according to the fourth embodiment. In this modification, inner balloon 126, which has no rib on its outer peripheral surface, is attached to the distal end portion of porous tube 8. The outer peripheral surface of balloon 126 is surrounded by elastic metal net member 134. Member 134 is connected with electric wire 132 which is inserted in feed passage 118. A combination of net member 134 and an electrically conductive solution in space 130 is used as an internal electrode.

In this modification, the metal net member serves as part of the internal electrode, the warming effect between the internal and external electrodes, and the inner balloon is prevented from excessively expanding by the net member.

Figure 18:
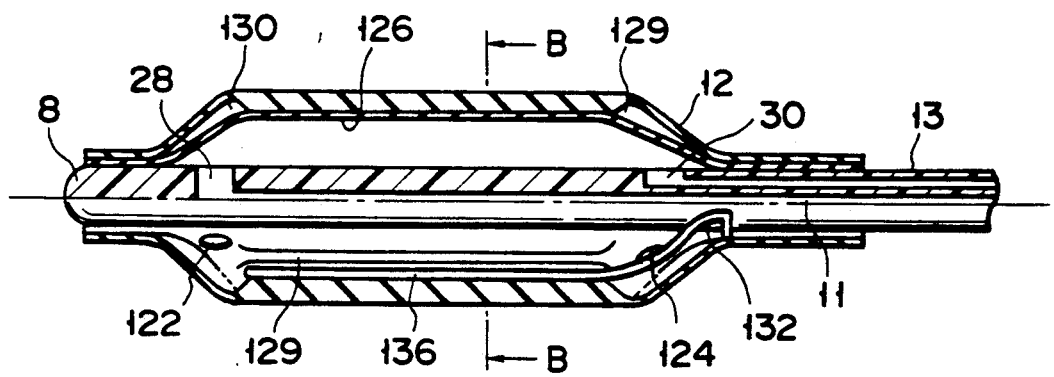
FIG. 18 is a partial sectional view showing a second modification of the internal applicator according to the fourth embodiment.
Figure 19:
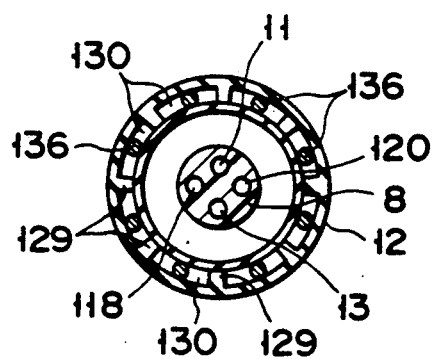
FIG. 19 is a cross-sectional view taken along line B-B of FIG. 18.

FIGS. 18 and 19 show a second modification of the internal applicator. In this modification, inner balloon 126, which has no rib on its outer peripheral surface, is attached to the distal end portion of porous tube 8. The outer peripheral surface of balloon 126 is enclosed by outer balloon 12, and a plurality of axially extending ribs 129 are arranged circumferentially at regular intervals on the inner surface of outer balloon 12. Each end of each rib 129 extends shorter than its corresponding end of balloon 12. All of elongate spaces 130 defined between adjacent ribs 129 communicate with one another. Needle electrode 136 is contained in each space 130, and is connected with each corresponding electric wire 132. In the internal applicator according to this modification, balloons 126 and 12 can be more easily expanded and contracted.

The conductive solution in spaces 130 may be previously injected before internal applicator 4 is inserted into body cavity 80, or be circulated between a feeding device and the internal applicator. In the thermotherapeutic apparatus according to the fourth embodiment, the conductive solution, for use as the internal electrode, touches the tissues of the patient's body across the first balloon. Thus, the internal electrode can enjoy good contact with the body tissues.

Since the refrigerant circulates on the inner side of the internal electrode, high-frequency energy can not be absorbed by the refrigerant. Thus, the warming effect between the internal and external electrodes and the cooling effect of the refrigerant can never be lowered.

In the above embodiments, the present invention has been applied to the RF thermo-therapy. However, this invention is applicable to a microwave thermo-therapy. In this case, an external applicator is not needed. If an internal applicator is employed as an antenna, from which microwaves are irradiated on a diseased part of the body, the thermo-therapy can be achieved.

What is claimed is:

1. A thermotherapeutic apparatus comprising:
   a first elongated applicator adapted to be inserted along its direction of elongation into a body cavity, said first applicator including first electrode means for warming tissues of a living body with use of an applied voltage;
   holding means disposed inside the first electrode means for holding the first electrode means thereon;
   a first balloon surrounding the first electrode means and attached to the holding means;
   feed/discharge means for feeding into and discharging a fluid from the first balloon;
   means for selectively loading and removing a radiation source, used in radiotherapy on the body tissues, into and from an inner space in the holding means from outside of said body cavity; and
   means for situating the radiation source in the inner space of the holding means so that a distal end of the first electrode means extends, in said direction of elongation, at least to a distal end of the radiation source.

2. The thermotherapeutic apparatus according to claim 1, further comprising a second applicator adapted to be disposed outside the living body, said second applicator including second electrode means for warming the tissues, in cooperation with the first electrode means.

3. The thermotherapeutic apparatus according to claim 1, further comprising voltage supply means for applying a pulse voltage to the first electrode means, and control means for detecting the temperature of the first electrode means and feedback-controlling the pulse voltage.

4. The thermotherapeutic apparatus according to claim 1, further comprising means for electrically insulating the first electrode means from the fluid fed into the balloon.

5. The thermotherapeutic apparatus according to claim 1, further comprising a second balloon disposed in the first balloon and attached to the holding means.

6. The thermotherapeutic apparatus according to claim 5, wherein said first electrode means is disposed in a space defined between the first and second balloons.

7. The thermotherapeutic apparatus according to claim 5, wherein said first electrode means includes an electrically conductive solution fed into a space defined between the first and second balloons.

8. The thermotherapeutic apparatus according to claim 5, further comprising prevention means disposed between the first and second balloons and adapted to prevent the second balloon from expanding excessively.

9. The thermotherapeutic apparatus according to claim 1, wherein the situating means situates the radiation source along said direction of elongation between the distal end and a proximal end of said first electrode means.

10. The thermotherapeutic apparatus according to claim 9, wherein the situating means centers the radiation source, along said direction of elongation, between said distal and proximal ends of said first electrode means.

11. The thermotherapeutic apparatus according to claim 10, wherein the first electrode means and the radiation source are centered, along said direction of elongation, in said first balloon.

12. The thermotherapeutic apparatus according to claim 1, wherein the said holding means comprises a multi-lumen tube.

13. A thermotherapeutic apparatus comprising:
a first applicator adapted to be inserted into a body cavity, said first applicator including an elongate member having a plurality of fluid passages, a first balloon attached to a distal end portion of the elongate member, a second balloon disposed in the first balloon and attached to the elongate member, feed/discharge means for feeding into and discharging a fluid from the second balloon through a first fluid passage of the elongate member, and first electrode means disposed between the first and second balloons and adapted to warm tissues of a living body with use of an applied voltage.

14. The thermotherapeutic apparatus according to claim 13, further comprising a second applicator adapted to be disposed outside the living body, said second applicator including second electrode means for warming the tissues, in cooperation with the first electrode means.

15. The thermotherapeutic apparatus according to claim 13, wherein said first electrode means includes an electrically conductive solution fed through a second fluid passage of the elongate means into a space defined between the first and second balloons.

16. The thermotherapeutic apparatus according to claim 13, further comprising prevention means disposed between the first and second balloons and adapted to prevent the second balloon from expanding excessively.

17. The thermotherapeutic apparatus according to claim 13, further comprising voltage supply means for applying a pulse voltage to the first electrode means, and control means for detecting the temperature of the first electrode means and feedback-controlling the pulse voltage.

18. An internal applicator of a thermotherapeutic apparatus, comprising:
heat generating means for warming tissues of a living body;
holding means for holding the heat generating means;
a first balloon surrounding the heat generating means and attached to the holding means;
feed/discharge means for feeding into and discharging a fluid from the first balloon; and
means for situating a radiation source, used in radiotherapy on the tissues, in the vicinity of the heat generating means.

19. The internal applicator of a thermotherapeutic apparatus according to claim 18, further comprising voltage supply means for applying a pulse voltage to the heat generating means, and control means for detecting the temperature of the heat generating means and feedback-controlling the pulse voltage.

20. The internal applicator of a thermotherapeutic apparatus according to claim 18, further comprising means for electrically insulating the heat generating means from the fluid fed into the balloon.

21. The internal applicator of a thermotherapeutic apparatus according to claim 18, further comprising a second balloon disposed in the first balloon and attached to the holding means.

22. The internal applicator of a thermotherapeutic apparatus according to claim 21, wherein said heat generating means is disposed in a space defined between the first and second balloons.

23. The internal applicator of a thermotherapeutic apparatus according to claim 21, wherein said heat generating means includes an electrically conductive solution fed into a space defined between the first and second balloons.

24. The internal applicator of a thermotherapeutic apparatus according to claim 21, further comprising prevention means disposed between the first and second balloons and adapted to prevent the second balloon from expanding excessively.

* * * * *